United States Patent [19]
Loncar

[11] Patent Number: 5,613,391
[45] Date of Patent: Mar. 25, 1997

[54] MACHINE AND METHOD FOR KNURLING THE TIP OF A NEEDLE

[76] Inventor: Stanley M. Loncar, 10130 S. Nicholson Rd., Oak Creek, Wis. 53154

[21] Appl. No.: 399,076

[22] Filed: Mar. 8, 1995

[51] Int. Cl.$^6$ ..................................... B21H 7/14
[52] U.S. Cl. ..................... 72/90; 163/5; 604/272; 72/703
[58] Field of Search ................. 72/88, 90, 703; 163/1, 5; 604/272, 274

[56] References Cited

U.S. PATENT DOCUMENTS

| | | | |
|---|---|---|---|
| 458,685 | 9/1891 | Morris | 72/88 |
| 1,161,586 | 11/1915 | Axmacher | 72/90 |
| 1,273,441 | 7/1918 | Bardwell | 72/88 |
| 2,020,659 | 11/1935 | Frost | 72/90 |
| 2,191,771 | 2/1940 | Olson | 72/88 |
| 2,411,932 | 12/1946 | Mitchell | 72/90 |
| 4,252,009 | 2/1981 | Grohoski | 72/90 |
| 4,869,259 | 9/1989 | Elkins | 604/272 |
| 5,201,760 | 4/1993 | West | 163/1 |

FOREIGN PATENT DOCUMENTS

| | | | |
|---|---|---|---|
| 1208820 | 1/1966 | Germany | 72/88 |
| 53855 | 2/1967 | Germany | 604/272 |
| 462646 | 3/1975 | U.S.S.R. | 72/90 |

*Primary Examiner*—Daniel C. Crane
*Attorney, Agent, or Firm*—Foley & Lardner

[57] ABSTRACT

A machine and method for knurling an end portion of a cylindrical workpiece including a hypodermic needle or biopsy needle. The machine includes a base to which a reciprocating mechanism and a serrated block are attached. A pressure bar is positioned above the base and has a second serrated block attached thereto. The pressure bar is reciprocated back and forth, each movement comprising a stroke. A pair of lobes are attached to the top surface of the pressure bar. A pair of roller blocks are also attached to the base, each roller block having a rectangular opening and a roller located therein. The pressure bar passes through the rectangular openings. As the pressure bar is reciprocated back and forth and the lobes come into contact with the rollers, the pressure bar is biased toward the base whereby a knurl is formed in a workpiece placed between the two serrated blocks. A method for knurling an end portion of a cylindrical workpiece is also disclosed.

9 Claims, 3 Drawing Sheets

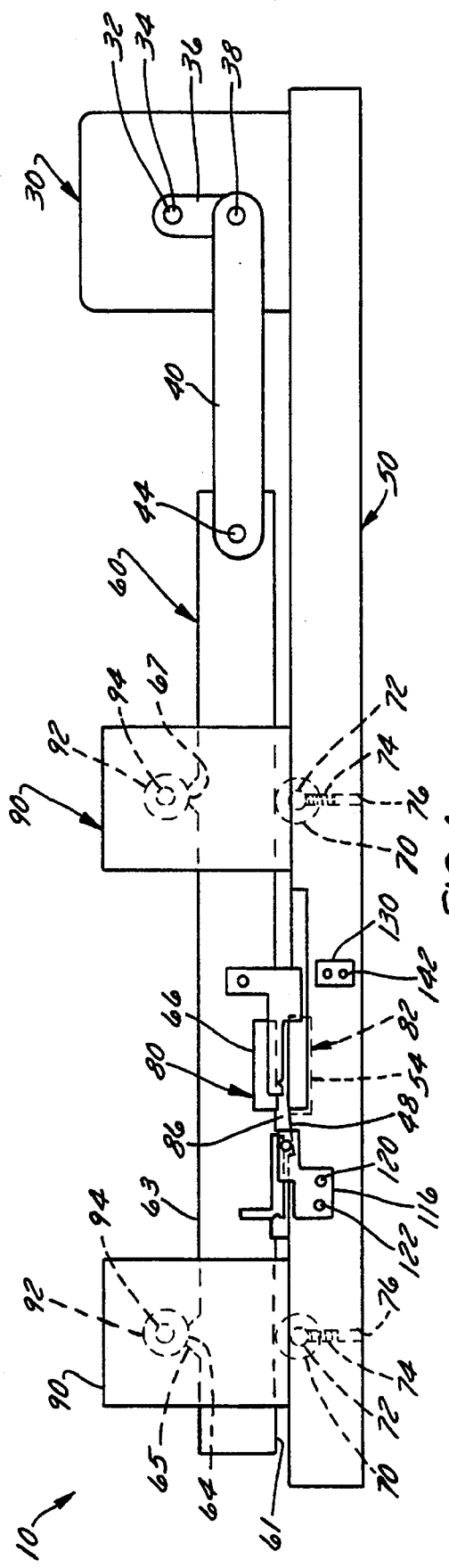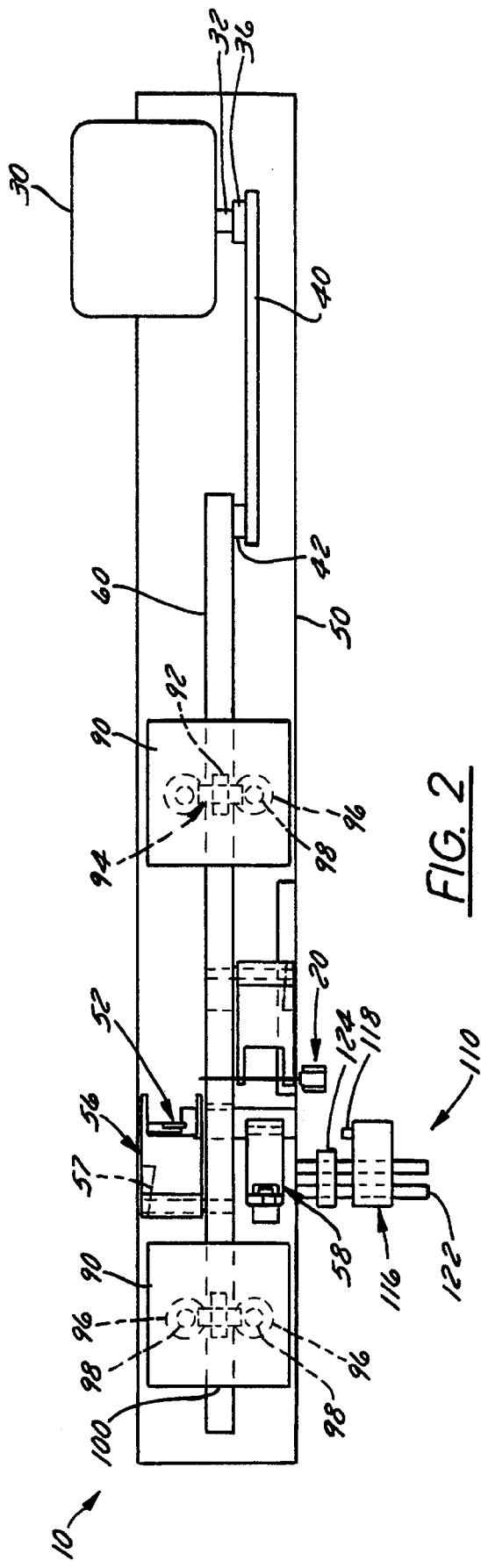

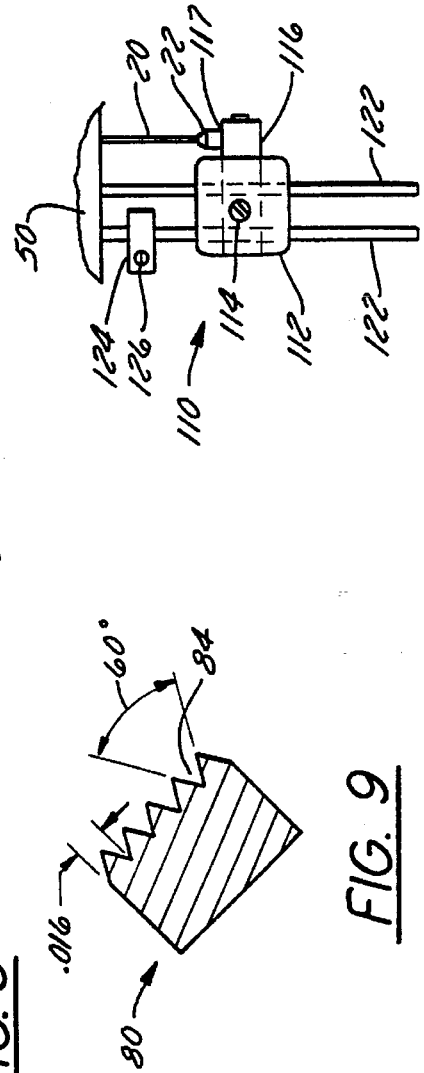

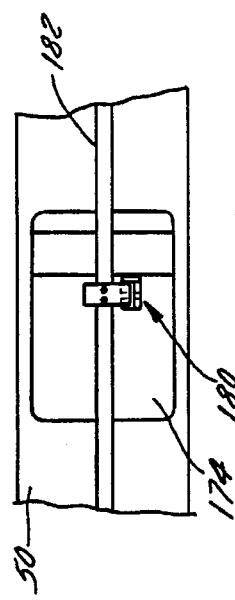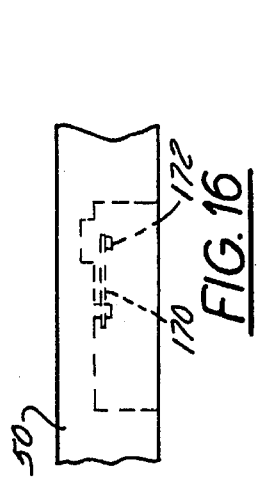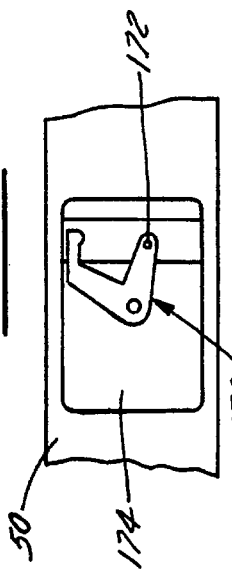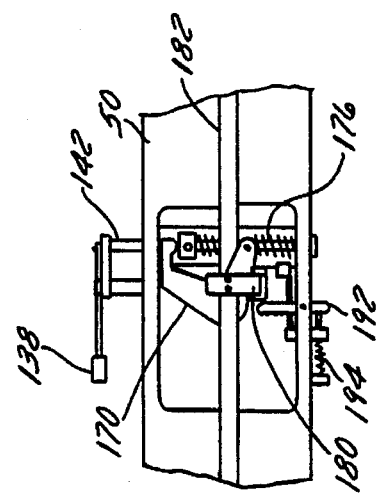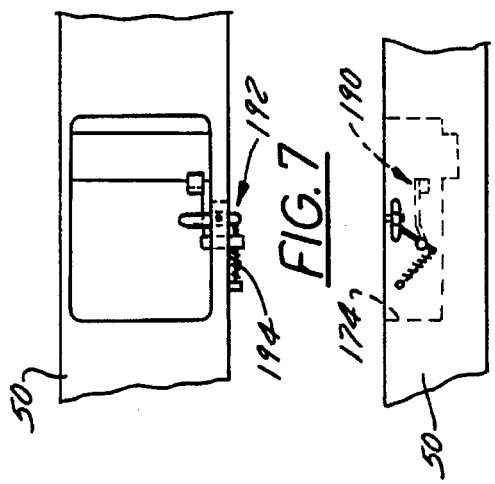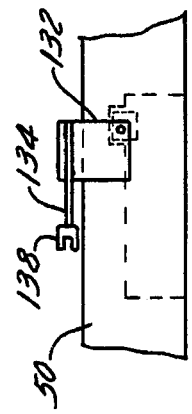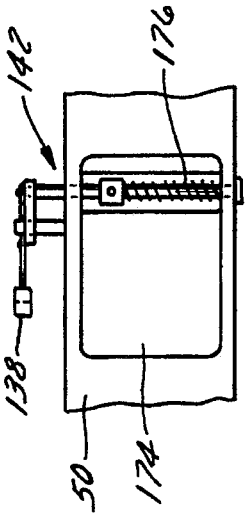

MACHINE AND METHOD FOR KNURLING THE TIP OF A NEEDLE

BACKGROUND OF THE INVENTION

The present invention relates generally to a machine and method for knurling cylindrical workpieces and specifically to a machine that knurles an end portion of a hypodermic or biopsy needle located adjacent to its tip. This knurling allows the tip of the needle to be more easily seen by medical imaging apparatus.

Often during a medical procedure, medical personnel utilize a laser or ultrasound apparatus for instantaneously viewing a particular organ or cavity within a patient. It is often necessary to remove a sample of tissue or fluid from the respective internal organ or cavity. To remove the required sample matter, a needle such as a hypodermic needle or a biopsy needle is inserted through the patient's skin and into the area where the sample matter is to be removed. When the end or tip of the needle is within the desired region, the sample matter is withdrawn through the needle and into the capturing apparatus, typically a syringe.

It is highly advantageous for the medical personnel to be able to view the needle, especially the needle tip, and know its exact location as it is inserted into the body cavity. In this way, when the needle tip enters the desired or targeted cavity or organ, the doctor knows that he or she is removing the desired matter from the patient because the location of the sampling end or needle tip may be seen in relation to the targeted area of the organ or cavity from which the sample is to be withdrawn. Without some type of visual aid, the doctor or medical technician must otherwise guess or estimate when the needle tip is correctly positioned within the cavity or organ and when is the proper time to withdraw the required fluid or tissue.

The smooth tip and body of a hypodermic or a biopsy needle does not produce a visible image on a laser or ultrasound monitor. Because the tip and body directly reflect the ultrasonic waves emitted by the machine in the same way, no differential is produced and the needle does not appear in the resulting image displayed on the monitor. By cutting or forming a knurl or pattern near the end or tip of a needle, the ultrasonic waves are not directly reflected in the same manner at the tip as at the body; a differential is produced. The knurled portion of the needle now becomes visible on the resulting image displayed on the screen or monitor. By knowing exactly where the knurled portion of the needle body is, the doctor can easily determine where the tip of the needle is with respect to the selected body cavity or organ which also appears on the monitor. Thus the doctor can be assured that he or she is withdrawing the desired matter from the patient and not matter from another organ, tumor, or body cavity. The guess work as to when the needle tip is properly located within the selected area of the patient's body is eliminated.

It is an object of the present invention to provide a machine and method for forming or cutting a knurl near the end of a cylindrical workpiece or hypodermic or biopsy needle. It is a further object to provide a machine that is of a simple construction and design. It is yet a further object to form or cut the knurl without supporting the cylindrical workpiece or needle on its ends during the knurling process. It is yet a further object to provide such a machine that correctly positions the workpiece within the machine, forms the knurl at the predetermined location, and automatically ejects the workpiece when the knurling process is complete.

Further, it is an object of the present invention to produce a knurled workpiece or needle by the process and machine disclosed herein. These and other objects of the present invention will become evident in the following descriptions The inventor knows of no prior art that teaches or discloses the present invention.

SUMMARY OF THE INVENTION

The invention comprises a machine and method for cutting a knurl or pattern on the end of a cylindrical workpiece or hypodermic needle or biopsy needle. The knurl or pattern produces a reflection differential that is visibly discernable by a laser or ultrasonic imaging apparatus. The invention comprises a base having a reciprocating mechanism attached at one end. A pair of base rollers are supported above the base by base roller springs. A pair of roller blocks are also attached to the base. Each roller block has a rectangular opening and an upper roller. The top surface of the pressure bar has two raised portions or lobes which come into contact with the upper rollers attached to the roller blocks during a portion of the pressure bar stroke. A pressure bar is positioned above and parallel to the base. The pressure bar passes through each rectangular opening in each roller block. The pressure bar is reciprocated back and forth on the base rollers by the reciprocating mechanism.

A pair of serrated blocks or cutting tools are located between the roller blocks. One serrated block is attached within the base while the other is attached to the pressure bar. The opposed facing surfaces of each serrated block are grooved on 45 degree angles in two directions. The grooves are cut at a 60 degree angle.

The reciprocating mechanism reciprocates the pressure bar back and forth, each movement being defined as a stroke. The bottom surface of the pressure bar rides on the spring-mounted rollers attached to the base. When the pressure bar lobes are not in contact with upper rollers connected to roller blocks, a gap is presented between the upper and lower serrated blocks. This gap allows the cylindrical workpiece or needle to be placed between the blocks. As the stroke begins, the pressure bar lobes encounter the upper rollers and the pressure bar is pushed down against the lower rollers riding on the base roller springs. As the pressure bar lobes pass under the upper rollers, the pressure bar and the serrated block attached to it are biased downward pressing the serrations of the serrated blocks into tangential contact with the needle. As the stroke continues, the needle rolls under pressure along the length of each block while the knurl is cut or formed and until the lobes are no longer in contact with the upper rollers. The pressure bar will then be biased back upward by the base roller springs and the knurled needle can be removed from the gap. In the preferred embodiment, a needle insertion mechanism and a needle ejection mechanism are also provided.

Alternatively, my invention can be described as a method for knurling a portion of a cylindrical workpiece, the method comprising the steps of placing a needle between a pair of serrated blocks, biasing one block toward to the other block, moving each block in opposite axial directions, unbiasing the blocks, and removing the needle.

DESCRIPTION OF THE DRAWINGS

FIG. 1 is a front view of the machine for knurling needles.

FIG. 2 is a top plan view of the machine for knurling needles.

FIG. 3 is a top plan view of a serrated block.

FIG. 4 is a top plan view of the needle insertion assembly.

FIG. 5 is an exploded view of the needle ejector assembly shown at 5 in FIG. 1.

FIG. 6 is a top plan view of the needle ejector assembly.

FIG. 7 is a bottom view of the trip lever mechanism.

FIG. 8 is a side view of the pivot arm lock mechanism.

FIG. 9 is a cut-away view of the serrated block taken at line 9—9 of FIG. 3.

FIG. 10 is perspective view of an end portion of a typical hypodermic or biopsy needle having a knurl formed therein.

FIG. 11 is a side view of the needle ejection mechanism.

FIG. 12 is a bottom view of the ejector slide mechanism.

FIG. 13 is a bottom view of the needle ejection mechanism.

FIG. 14 is a side view of the sliding cam mechanism.

FIG. 15 is a bottom view of the sliding cam mechanism.

FIG. 16 is a side view of the pivot arm mechanism.

FIG. 17 is a bottom view of the pivot arm mechanism.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

My invention, shown at 10 in FIGS. 1 and 2, comprises a machine and method for knurling the end portions of cylindrical workpieces, namely hypodermic and biopsy needles. Its primary components include a motor 30, a base 50, a pressure bar 60, roller blocks 90, and serrated blocks 80.

Motor 30 is attached to one end of base 50, as shown in FIG. 1, and has an output shaft 32. Output shaft 32 is coupled to crank arm 36 at coupling connection 34. The opposite end of crank arm 36 is pivotally connected to an end of link arm 40 at pivotable connection 38. The other end of link arm 40 is connected to pressure bar 60 at end 62. A pin 44 and washer 42, as shown in FIG. 2, are utilized.

When motor 30 is energized by a power source, its output shaft 32 rotates in either a clockwise or counterclockwise direction. This in turns rotates crank arm 36. At pivotable connection 38, the rotational motion produced by motor 30 is converted to a reciprocating motion imparted on link arm 40. Link arm 40 reciprocates pressure bar 60 back and forth in a substantially linearly motion. Each linear movement of link arm 40, either forward or backward, is a pressure bar stroke of the pressure bar 60.

The bottom side 61 of pressure bar 60 rides on base rollers 70. Base rollers 70 are rotatably mounted on base roller axles 72 which are supported by base roller springs 74. The base roller springs 74 are each located within base spring cavities 76 formed within base 50.

A lower serrated block cavity 54 is also formed in base 50 between the base spring cavities 76 as shown in FIG. 1. A lower serrated block 82, which forms the knurl or pattern on the workpiece or needle 20, is housed and held in place within cavity 54.

Referring to FIGS. 1 and 2, the roller blocks 90 are attached to base 50. Each roller block 90 is positioned above a base roller 70 and has a rectangular opening 100. Pressure bar 60 passes through each rectangular opening 100. Within each block 90, a pair of pressure bar guide rollers 96 are positioned to vertically support pressure bar 60. Each pressure bar guide roller 96 is in contact with pressure bar 60. The pressure bar guide rollers 96 are rotatably supported by pressure bar guide roller axles 98. The ends of the axles 98 are fixedly attached within roller blocks 90. Alternatively, the pressure bar guide rollers 96 could be fixedly attached to the roller axles 98 which could in turn rotate within roller blocks 90.

Near the top of each roller block 90 and perpendicular to the pressure bar guide rollers 96, an upper block roller 92 is rotatably mounted on an upper block roller axle 94. Each axle's ends are connected to and supported by roller block 90 in a manner similar to pressure bar guide roller axles 98.

An upper serrated block cavity 66 is formed within pressure bar 60 for retaining upper serrated block portion 80. Both upper serrated block 80 and lower serrated block 82 have identical knurling surfaces 84 as shown in FIGS. 3 and 9. Each surface 84 is grooved on a 45 degree angle in two directions. The grooves are cut at a 60 degree angle and are 0.016 inches (0.0406 cm) apart. The surface 84 of the serrated blocks 80 and 82 could be changed or modified to form a different knurl or knurling pattern without deviating from my invention as shown and described.

Referring to FIG. 1, a pair of pressure bar lobes 64 are formed on the upper surface 63 of pressure bar 60. Each lobe 64 is positioned such that each upper block roller 92 passes above each respective lobe 64 during a stroke of pressure bar 60.

During the beginning and ending portions of each pressure bar 60 stroke, base roller springs 74 bias base rollers 70 in an outward direction and elevate pressure bar 60 to its uppermost limit away from base 50. At these portions, upper surface 63 of pressure bar 60 is in rolling contact with upper block rollers 92. The gap 86 presented between upper and lower serrated blocks 80 and 82 is at its maximum. When fully opened, a needle 20 is placed within gap 86.

My invention 10 can perform a knurling operation during each stroke. The following description relates to knurling during the forward stroke (pressure bar 60 moving toward motor 30); knurling during the backward stroke (pressure bar 60 moving away from motor 30) is identical in operation.

Referring to FIGS. 1 and 2, needle 20 is placed in gap 86 during the end of the backward stroke when the upper block rollers 92 are off of pressure bar lobes 64 but feed finger 56 is still to the fight of needle 20. The tip 24 and body 26 of needle 20 are placed under needle hold down bar 58 until the needle tip 24 contacts adjustable needle stop 52. Adjustable needle stop 52 comprises an aluminum pin having a predetermined length to correctly position needle body 26 with respect to serrated blocks 80 and 82. As feed finger 56 returns, the wedge shaped locator 57 on its bottom side pushes adjustable stop or pin 52 securely against needle tip 24 and slides needle 20 to the proper position for knurl 28 length on needle body 26.

Needle 20 stays in position under hold down bar 58 as pressure bar 60 continues its backward stroke. At the end of the backward stroke, feed finger 56 grabs needle 20. As pressure bar 60 starts to move forward, feed finger 56 slides needle 20 up ramp 48 on base 50 and onto the loading edge of lower serrated block 82.

As the stroke of the pressure bar 60 continues, upper block rollers 92, presently riding on surface 63 encounter pressure bar lobes 64. Each pressure bar lobe 64 has an inclined surface 65. As the stroke continues, upper block rollers 92 ride up incline surfaces 65 and onto top surfaces 67 of each respective lobe 64 as shown in FIG. 1. This biases pressure bar 60 toward base 50 and begins to close or narrow gap 86. As gap 86 begins to close, the opposite tangential surfaces of needle 20 come into contact with each respective serrated block 80 or 82. As the stroke of pressure bar 60 continues, the needle body 26 of needle 20 is rolled approximately three (3) times between serrated blocks 80 and 82. The rolling action forms or cuts a knurl 28 on the needle body 26 as shown in FIG. 10. Preferably, the knurl or pattern 28 is formed as close to tip 24 as possible without distorting the structure of the tip 24.

When the upper block rollers 92 have completely rolled across top surface 67 of lobe 64 and down the opposite inclined surface 65, pressure bar 60 is again biased outward by base roller springs 74 and gap 86 is opened. Once opened, needle 20 can be removed from machine 10.

An optional needle insertion assembly 110 and needle ejection assembly 130 are provided. The needle insertion assembly 110 includes a handle 112, sliding feeder bar 116 having a guide pin 118, a pair of guideposts 122 and an adjustable guide stop 124.

As shown in FIG. 4, the pair of guideposts 122 are connected to and project from base 50. Sliding feeder bar 116 has two openings 120 having bearing surfaces for receiving guideposts 122. Sliding feeder bar 116 slides in a linear manner on posts 122. A guide pin 118 is attached to side 117 of feeder bar 116. The guide pin 118 is sized to receive and hold the needle base 22 of needle 20. Needle base 22 is that portion of needle 20 that connects to the syringe body. A handle 112 is attached by fastener 114 to the top of needle guide 116. An adjustable needle stop 124 is provided on one or both guideposts 122. The adjustable stop 124 includes a fastener 126 which is loosened to change the position of the needle stop 124 and then retightened to hold needle stop 124 in the selected location.

The needle insertion assembly 110 is used as follows: In its fully retracted position, a needle 20 is placed on sliding feeder bar 116 by placing needle base 22 over guide pin 118. The operator next grabs handle 112 and slides feeder bar 116 on guideposts 122 so that the body 26 of the needle 20 enters the gap 86 presented between he serrated blocks 80 and 82. The handle 112 is pushed forward until the needle tip 24 encounters adjustable stop 52 located on the opposite side of gap 86 and until feeder bar 116 contacts adjustable stop 124. When the needle 20 has been fully inserted, the handle 112 and guide 116 are retracted. When retracted, the needle 20 remains in gap 86. The next needle 20 can then be loaded onto guide pin 118.

Referring to FIGS. 5 and 6, the needle ejection assembly 130 includes an ejector body 132, an ejector arm 134, a needle receiver 138, an ejector shaft 140, a spring loaded ejector slide 142, and an ejecting mechanism 150. Ejector shaft 140 also projects outward from base 50. Ejector body 132 slides on ejector shafts 140. The ejector arm 134 is connected at one end to ejector body 132 by fasteners 136. The needle receiver 138 is attached to the other end of the ejector arm 134. Needle receiver 138 has a pair of arms 139 sized and spaced to receive a needle body 26 where it meets needle base 22. The gap between arms 139 is smaller than the diameter of the needle base 22.

Spring loaded ejector slide 142 is attached to an ejecting mechanism 150 shown best in FIG. 13. The mechanism 150 includes the spring loaded ejector slide 142, a pivot arm 170 having a pin 172, a sliding cam 180 attached to sliding shaft 182, a pivot arm lock 190, and a trip lever 192. The sliding shaft 182 is located within base 50 and is attached to the pressure bar 60 and reciprocates back and forth with pressure bar 60. A cavity 174 is formed within base 50. The components of the ejecting mechanism 150 are housed within the cavity 174.

As the pressure bar 60 travels forward, sliding cam 180, which is attached to sliding shaft 182, moves forward and passes over pin 172 on pivot arm 170. As pressure bar 60 and sliding cam 180 begins to move in the opposite direction, the sliding cam 180 pulls pivot arm 170 thereby compressing spring 176 on ejector slide 142 and retracting ejector slide 142. The sliding cam 180 next pulls pivot arm pin 172 which slides pivot arm lock 190 up and over pin 172 holding pivot arm 170 in place. The sliding cam 180 continues its travel past trip lever 192. Trip lever 192 is biased into position by trip lever spring 194.

As the pressure bar 60 travels forward again, sliding cam 180 strikes trip lever 192 again this time releasing pivot arm lock 190. This releases pivot arm 170 and spring loaded ejector slide 142 is biased outward by compressed spring 176. As ejector slide 142 moves outwardly, the workpiece or needle 20 is ejected from the machine 10.

The needle ejection assembly 130 works as follows: As pressure bar 60 continues its stroke, needle 20 is rolled linearly between the serrated blocks 80 and 82 which form the knurl 28 on the needle body 26. Near the end of the stroke, the needle body 26 enters needle receiver 138 between its pair of arms 139. When the stroke is complete, gap 86 opens and needle 20 is no longer confined between serrated blocks 80 and 82. At or after that moment, ejector shafts 142 move outward from body 50. In turn, ejector body 132, ejector arm 134, and needle receiver 138 are moved outward. Needle 20 is withdrawn from machine 10 by needle receiver 138 and deposited into a collection bin located beneath needle ejection assembly 130.

Alternatively, my invention comprises a method for knurling an end portion of a cylindrical workpiece or hypodermic needle or biopsy needle 20. The method comprises the steps of placing an end portion 29 of the workpiece 20 between a pair of blocks 80 and 82 having serrated surfaces 84, biasing the serrated surfaces 84 toward each other, moving the blocks 80 and 82 in opposite axial directions, unbiasing the blocks 80 and 82, and removing the needle 20.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. An apparatus for forming a knurl on an end portion of a needle, the apparatus comprising:

a base;

a pressure bar having at least two pressure bar lobes;

a reciprocating mechanism having one end attached to the base and the other end attached to the pressure bar;

a first serrated knurling block attached to the base and a second serrated knurling block attached to the pressure bar wherein said first and second knurling blocks are opposingly disposed to create a needle receiving void therebetween;

a pair of upwardly biased base rollers rotatably attached to the base;

a pair of roller blocks fixedly attached to the base, each block having an opening and an upper roller;

the pressure bar supported by the upwardly biased rollers and passing through the roller block openings wherein the roller blocks are biased against the lobes to impel the second block toward the first block.

2. The apparatus of claim 1 wherein the reciprocating mechanism comprises:

a motor having an output shaft;

a crank arm having a first crank arm end and a second crank arm end, the first crank arm end connected to the output shaft;

a link arm having a first link arm end and a second link arm end, the first link arm end rotatably connected to the second crank arm end;

the second link arm end pivotally connected to the pressure bar.

3. The apparatus of claim 1 further including a needle insertion mechanism, the mechanism comprising:

at least one guide post attached to the base;

a needle guide having a guide pin adapted to support and insert the needle and at least one guide post bearing, the guide post receiving the guide post bearing;

a handle attached to the needle guide wherein the needle guide is adapted to slidingly advance on the guide post toward the needle receiving void.

4. The apparatus of claim 1 further including a needle ejection mechanism, the mechanism comprising:

at least one ejector shaft capable of moving in an outward direction supported by the base;

an ejector body attached to the ejector shaft;

an ejector arm having a needle receiver, the ejector arm attached to the ejector body adapted to support and elect the needle.

5. An apparatus for knurling an end portion of a needle, the apparatus comprising:

a base having a first end, a second end, and a mid section;

a first tool having a first serrated knurling surface attached to the base between the first end and the mid section;

a reciprocating mechanism attached to the second end of the base;

a pressure bar having an end, a top surface, and a bottom surface;

a second tool having a second serrated knurling surface attached to the pressure bar bottom surface and opposingly disposed to the first serrated knurling surface to create a needle receiving void therebetween;

two pressure bar lobes attached to the pressure bar top surface;

a first spring mounted roller and a first roller block attached to the mid section of the base and a second spring mounted roller and a second roller block attached to the first end of the base;

each roller block having a rectangular opening and a roller block roller rotatably mounted therein;

the pressure bar passing through each rectangular opening in each roller block and the pressure bar bottom surface being in rolling contact with each spring mounted roller wherein the roller blocks are biased against the lobes to impel the second knurling surface toward the first knurling surface.

6. The apparatus of claim 5 wherein the reciprocating mechanism comprises:

a motor having an output shaft;

a crank arm having a first crank arm end and a second crank arm end, the first crank arm end connected to the output shaft;

a link arm having a first link arm end and a second link arm end, the first link arm end rotatably connected to the second crank arm end;

the second link arm end pivotally connected to the pressure bar.

7. The apparatus of claim 5 further including a needle insertion mechanism, the mechanism comprising:

at least one guide post attached to the base;

a needle guide having a guide pin and at least one guide post bearing, the guide post receiving the guide post bearing;

a handle attached to the needle guide.

8. The apparatus of claim 5 further including a needle ejection mechanism, the mechanism comprising:

at least one ejector shaft, capable of moving in an outward direction, supported by the base;

an ejector body attached to the ejector shaft;

an ejector arm having a needle receiver, the ejector arm attached to the ejector body.

9. A method for knurling an end portion of a needle, the method comprising the steps of:

placing the end portion of the needle between two serrated blocks;

biasing the blocks toward one another a predetermined distance and until each makes tangential contact with the end portion of the needle;

moving at least one of the blocks relative to the other of the blocks in a direction perpendicular to the longitudinal axis of the needle to thereby knurl the needle;

unbiasing the blocks;

removing the needle.

* * * * *